(12) United States Patent
Thulin

(10) Patent No.: US 12,427,140 B2
(45) Date of Patent: Sep. 30, 2025

(54) 4-[5-[(RAC)-1-[5-(3-CHLOROPHENYL)-3-ISOXAZOLYL]ETHOXY]-4-METHYL-4H-1,2,4-TRIAZOL-3-YL]PYRIDINE FOR USE IN PREVENTION AND/OR TREATMENT OF PAIN IN AN ANIMAL

(71) Applicant: Claes Thulin, Stockholm (SE)

(72) Inventor: Claes Thulin, Stockholm (SE)

( * ) Notice: Subject to any disclaimer, the term of this patent is extended or adjusted under 35 U.S.C. 154(b) by 893 days.

(21) Appl. No.: 17/604,750

(22) PCT Filed: Nov. 22, 2019

(86) PCT No.: PCT/EP2019/082264
§ 371 (c)(1),
(2) Date: Oct. 18, 2021

(87) PCT Pub. No.: WO2020/228973
PCT Pub. Date: Nov. 19, 2020

(65) Prior Publication Data
US 2022/0040165 A1     Feb. 10, 2022

(30) Foreign Application Priority Data
May 15, 2019 (SE) .................... 1950579-1

(51) Int. Cl.
*A61K 31/4439* (2006.01)
*A61K 45/06* (2006.01)
*A61P 19/02* (2006.01)
*A61P 29/00* (2006.01)

(52) U.S. Cl.
CPC .......... *A61K 31/4439* (2013.01); *A61K 45/06* (2013.01); *A61P 19/02* (2018.01); *A61P 29/00* (2018.01)

(58) Field of Classification Search
CPC .......................... C07D 413/14; A61K 31/4439
See application file for complete search history.

(56) References Cited

U.S. PATENT DOCUMENTS 7,476,684 B2    1/2009   Minidis et al.

FOREIGN PATENT DOCUMENTS

| KR | 20080050421 A | 6/2008 | |
|----|---|---|---|
| WO | 2004024074 A2 | 3/2004 | |
| WO | 2004089308 A2 | 10/2004 | |
| WO | WO-2007040982 A1 * | 4/2007 | ............. A61K 31/00 |

OTHER PUBLICATIONS

Hulikal, Deuterium Labeled Compounds in Drug Discovery Process, Abstract, 2010.*
Pimlott, PubMed Abstract (Nucl Med Commun., 26(3):183-8), 2005.*
Tranquilli, NAVC Conference 2010, Small Animal Pain Management (Year: 2010).*
Hellyer, Management of Chronic Pain in the Dog and Cat, Hellyer, P.W, Conference Proceedings 2003 (Year: 2003).*
WebMD , Rheumatoid Arthritis vs. Osteoarthritis: What's the Difference?, 2024, url=https://www.webmd.com/rheumatoid-arthritis/rheumatoid-arthritis-osteoarthritis-difference, accessed Jul. 24, 2025 (Year: 2024).*
Vincent, Nature Communications, 7, article No. 10604, 2016 (Year: 2016).*
Office Action in Related Case in CN Issued on Jun. 15, 2023 including English Translation.
English Translation of Office Action in Related Case in JP on Aug. 29, 2023.
Office Action in Related Case in CN Issued on Nov. 30, 2023 including English Translation.
"Genomic responses in mouse models poorly mimic human inflammatory diseases", PNAS, vol. 110, No. 9, Feb. 26, 2013 (Feb. 26, 2013), pp. 3507-3512.
Budsberg Sctorres Btkleine Sasandberg Gsberjeski Ak: "Lack of effectiveness of tramadol hydrochloride for the treatment of pain and joint dysfunction in dogs with chronic osteoarthritis", J Am Vet Med Assoc., vol. 252, No. 4, Feb. 15, 2018 (Feb. 15, 2018), pp. 427-432.
Court MH: "Feline drug metabolism and disposition: pharmacokinetic evidence for species differences and molecular mechanisms", Vet Clin North Am Small Anim Pract., vol. 43, No. 5, Sep. 2013 (Sep. 1, 2013), pp. 1039-1054.
Henze et al. "Large Animal Models for Pain Therapeutic Development", 2010.
Shrestha B et al.: "Evolution of a major drug metabolizing enzyme defect in the domestic cat and other felidae: phylogenetic timing and the role of hypercarnivory", Life Sci., vol. 79, No. 26, Nov. 25, 2006 (Nov. 25, 2006), pp. 2463-2473.
Tanaka N et al.: "cDNA cloning and characterization of feline CYP1A1 and CYP1A2", Life Sci., vol. 79, No. 26, Nov. 25, 2006 (Nov. 25, 2006), pp. 2463-2473, XP028051064, DOI: 10.1016/j.lfs.2006.09.030.
Blackburn-Munro, Pain-like behaviours in animals—how human are they?, Trends in Pharmacological Sciences, vol. 25, Issue 6, p. 299-305, Jun. 1, 2004.
International Written Opinion in PCT/EP2019/082264 Mailing Date Nov. 19, 2020.
International Search Report in PCT/EP2019/082264 Mailing Date Nov. 19, 2020.
International Preliminary Report on Patentability in PCT/EP2019/082264 Mailing Date Aug. 13, 2021.
Office Action in Related Case in CA Issued on Aug. 9, 2024.
Office Action in Related Case in MX Issued on Jul. 8, 2024 including English Translation.

(Continued)

*Primary Examiner* — Jeffrey H Murray
*Assistant Examiner* — Luisalberto Gonzalez
(74) *Attorney, Agent, or Firm* — Welsh IP Law LLC

(57) ABSTRACT

The present invention relates to 4-[5-[(rac)-1-[5-(3-Chlorophenyl)-3-isoxazolyl]ethoxy]-4-methyl-4H-1,2,4-triazol-3-yl]pyridine (TT00), or a pharmaceutically acceptable salt thereof, diastereomer, enantiomer, isotope, pro-drug or metabolite or mixture thereof, or a pharmaceutical composition comprising said TT00, for use in prevention and/or treatment of pain, such as chronic and/or peripheral pain and/or pain related to arthritis, such as osteoarthritis, or for use in prevention and/or treatment of said pain combined with b) GERD or c) anxiety in animals, such as dogs, cats or horses.

21 Claims, No Drawings

(56) References Cited

OTHER PUBLICATIONS

Office Action in Related Case in MX Issued on Jul. 10, 2024.
Office Action in Related Case in BR Issued on Aug. 7, 2024 including English Translation.
Office Action in Related Case in KR Issued on Nov. 25, 2024—including KR to EN translation.

* cited by examiner

4-[5-[(RAC)-1-[5-(3-CHLOROPHENYL)-3-ISOXAZOLYL]ETHOXY]-4-METHYL-4H-1,2,4-TRIAZOL-3-YL]PYRIDINE FOR USE IN PREVENTION AND/OR TREATMENT OF PAIN IN AN ANIMAL

FIELD OF THE INVENTION

The present invention relates to 4-[5-[(rac)-1-[5-(3-Chlorophenyl)-3-isoxazolyl]ethoxy]-4-methyl-4H-1,2,4-triazol-3-yl]pyridine (TT00), or a pharmaceutically acceptable salt thereof, diastereomer, enantiomer, isotope, pro-drug or metabolite or mixture thereof, or a pharmaceutical composition comprising said TT00, for use in prevention and/or treatment of pain, such as chronic and/or periferal pain and/or pain related to arthritis, such as osteoarthritis, or for use in prevention and/or treatment of said pain combined with b) GERD or c) anxiety in animals, such as dogs, cats or horses.

BACKGROUND

Pain is an area of major interest in veterinary medicine. The most commonly used pain relief for dogs is the use of nonsteroidal anti-inflammatory drugs (NSAIDs). However, long-term treatment with NSAID in cases of osteoarthritis will cause mayor side effects. Today, NSAIDs are used in 75% of the animals suffering from osteoarthritis in the EU.

Typical side effects for NSAIDs in dogs are vomiting, loss of appetite, depression and diarrhea. There are also serious side effects, such as gastrointestinal ulcer, liver/kidney failure, and even death have been reported.

TT00, or 4-[5-[(rac)-1-[5-(3-Chlorophenyl)-3-isoxazolyl]ethoxy]-4-methyl-4H-1,2,4-triazol-3-yl]pyridine

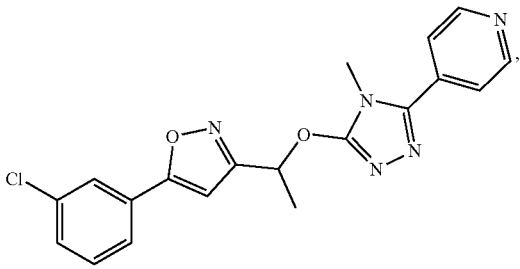 [SMILES: CC(Oc1nnc(-c2ccncc2)n1C)c1cc(-c2cccc(Cl)c2)on1]

and TT002, or 4-[5-[(1S)-1-[5-(3-Chlorophenyl)-3-isoxazolyl]ethoxy]-4-methyl-4H-1,2,4-triazol-3-yl]pyridine

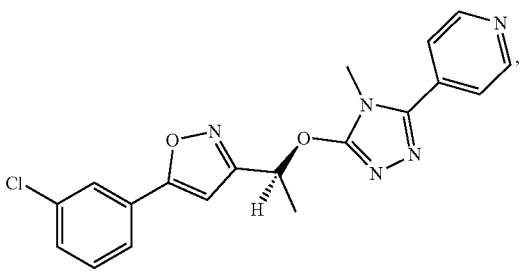

and

TT001, or 4-[5-[(1R)-1-[5-(3-Chlorophenyl)-3-isoxazolyl]ethoxy]-4-methyl-4H-1,2,4-triazol-3-yl]pyridine, CAS Number 934282-55-0,

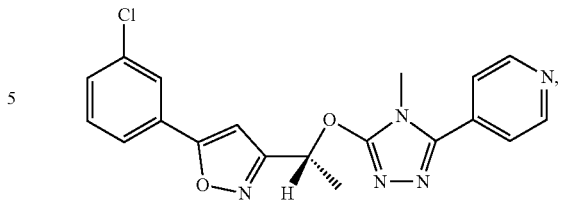

have a molecular formula $C_{19}H_{16}ClN_5O_2$ and a relative molecular mass of 381.8 (base).

These compounds are a selective non-competitive antagonists at metabotropic glutamate receptors subtype 5 (mGluR5), and developed for the oral treatment of chronic pain syndromes of neuropathic origin, anxiety and gastroesophageal reflux disease (GERD) in man. The developments for all indications were discontinued after clinical trials.

TT00 has an effect on the mGluR5 receptor in the central nervous system, which results in a central pain relief. Arthritis, such as osteoarthritis cause pain in the peripheral nervous system.

In clinical development, dogs are used for toxicity studies, but no efficacy studies have been performed on the pain indication. Bibliographic searches do not find any disclosures of treatment of pain or treatment of combinations of pain and anxiety or pain and GERD in dogs, cats or horses for said molecules.

Although animal models in rodents may be predictive for the effect in man, no studies have been presented, where rodent models predict the outcome in dogs. There are few pain models for larger animals.

Species Metabolite Comparison

Before a molecule becomes a drug candidate, many things must be cleared. Two important steps that the molecule must pass is the species compatibility by metabolite profile evaluation.

In the non-clinical part of drug development, studies are designed to determine the metabolite profiles and characterize selected metabolites that are generated following incubations of a molecule in rat and human hepatocytes. The results obtained are used to compare hepatic metabolism in man to that of the rodent model used in safety studies.

One method used is taking rat and human hepatocytes and incubate them with the molecule. The metabolite profiles in the supernatants will be recorded by liquid chromatography. Selected metabolites will be characterized by accurate mass spectrometry. There could be more than 10 different metabolites from the hepatic metabolism.

The metabolite profile should be similar between the two species. If this is not the case then the predictability of rodent models for man is not obvious and most probably the molecule will not be developed further.

It is also well known that for certain indications, like inflammatory diseases, the predictability of rodent models for man is very poor. (PNAS|Feb. 26, 2013|vol. 110|no. 9|3507-3512, Genomic responses in mouse models poorly mimic human inflammatory diseases).

This is also true for clinical pain. Unfortunately, there are many ways that the biology of rodents may fail to accurately predict the biology and pharmacology of clinical pain conditions in humans. (Blackburn-Munro 2004; Le Bars et al. 2001, Translational Pain Research: From Mouse to Man. Kruger L, Light A R, editors. Boca Raton, FL: CRC Press/Taylor & Francis; 2010. Chapter 17 Large Animal Models for Pain Therapeutic Development, Darrell A. Henze and Mark O. Urban).

Based on the difficulty to predict both the metabolism of a drug and the metabolite profile between species and the response in man based on rodent models, a person skilled in the arts will not be able to predict the efficacy and toxicity of a drug for one species based on data from another species, unless specific studies are conducted to verify the activity of the compound in the relevant species.

Furthermore, there are no published data relating to TT001 and the hepatic metabolism and metabolite profiles in rat and dog, and surely not for rat compared to cat and horse.

Examples of drugs that have different effect in different species are many.

Tramadol is widely used as a pain killer with good efficacy in man, the effect in dogs however do not occur. (J Am Vet Med Assoc. 2018 Feb. 15; 252(4): 427-432. doi: 10.2460/javma.252.4.427., Lack of effectiveness of tramadol hydrochloride for the treatment of pain and joint dysfunction in dogs with chronic osteoarthritis, Budsberg S C, Torres B T, Kleine S A, Sandberg G S, Berjeski A K.)

It is also known that tramadol has an adverse effect that can cause the dog to lose concept and balance, giving the impression that it is "high". There are also drugs that are used in man that are toxic to animals. An example of this is phenolic drugs, including acetaminophen and aspirin that should not be given to cats. (Shrestha B, et al., Evolution of a major drug metabolizing enzyme defect in the domestic cat and other felidae: phylogenetic timing and the role of hypercarnivory, Life Sci. 2006 Nov. 25; 79(26): 2463-73. Epub 2006 Oct. 5).

Court M H, Feline drug metabolism and disposition: pharmacokinetic evidence for species differences and molecular mechanisms, Vet Clin North Am Small Anim Pract. 2013 September; 43(5): 1039-54. doi: 10.1016/j.cvsm.2013.05.002, shows in FIG. 1 pharmacokinetic evidence for differences in drug elimination rates between cats, dogs, and humans. Shown is a comparison of published elimination half-life values in cats, dogs and humans for representative drugs that are primarily eliminated by conjugation (glucuronidation, sulfation, and glycination), oxidation (CYP enzymes) or are excreted primarily unchanged into urine and/or bile. All values are expressed as a ratio of the human value. Complete pharmacokinetic data and literature references are given in Table 1 for acetylsalicylic acid, propofol, acetaminophen, carprofen and piroxicam.

Especially for NSAIDs, some can be more or less deadly, and others work well. One difficulty with NSAIDs is that both the deadly and the good NSAIDs can come from the same chemical group/class. A good example of this is Ibuprofen, which is a toxic substance for dogs and cats. Ibuprofen is a propionic acid derivative and belongs to the same chemical group as Ketoprofen, Vedaprofen and Carprofen, all of which are given to all animals.

Further examples are listed below.

Dog

NSAIDs (e.g. Advil, Aleve and Motrin)

While these medications are safe for people, even one or two pills can cause serious harm to a pet. Dogs, cats, birds and other small mammals (ferrets, gerbils and hamsters) may develop serious stomach and intestinal ulcers as well as kidney failure.

Acetaminophen (e.g. Tylenol)

When it comes to pain medications, acetaminophen (e.g. Tylenol) is certainly popular. Even though this drug is very safe, even for children, this is not true for pets, especially cats. One regular strength tablet of acetaminophen may cause damage to a cat's red blood cells, limiting their ability to carry oxygen. In dogs, acetaminophen leads to liver failure and, in large doses, red blood cell damage.

Antidepressants (e.g. Effexor, Cymbalta, Prozac, Lexapro)

While these antidepressant drugs are occasionally used in pets, overdoses can lead to serious neurological problems such as sedation, incoordination, tremors and seizures. Some antidepressants also have a stimulant effect leading to a dangerously elevated heart rate, blood pressure and body temperature. Pets, especially cats, seem to enjoy the taste of Effexor and often eat the entire pill. Unfortunately, just one pill can cause serious poisoning.

ADD/ADHD Medications (e.g. Concerta, Adderall, Ritalin)

Medications used to treat Attention Deficit Disorder/Attention Deficit Hyperactivity Disorder contain potent stimulants, such as amphetamines and methylphenidate. Even minimal ingestions of these medications by pets can cause life-threatening tremors, seizures, elevated body temperatures and heart problems.

Benzodiazepines and Sleep Aids (e.g. Xanax, Klonopin, Ambien, Lunesta)

These medications are designed to reduce anxiety and help people sleep better. However, in pets, they may have the opposite effect. About half of the dogs who ingest sleep aids become agitated instead of sedated. In addition, these drugs may cause severe lethargy, incoordination (including walking "drunk"), and slowed breathing in pets. In cats, some forms of benzodiazepines can cause liver failure.

Beta-Blockers (e.g. Tenormin, Toprol, Coreg)

Beta-blockers are used to treat high blood pressure, but small ingestions of these drugs may cause serious poisoning in pets. Overdoses can cause life-threatening decreases in blood pressure and a very slow heart rate.

Cat

Drugs that are toxic to cats are Acetaminophen (Tylenol), Aspirin, Ibuprofen (Advil, Motrin), Naproxen (Aleve, Anaprox), Antidepressants, ADD/ADHD Medication, Sleep Aids (Benzodiazepines, Xanax, Ambien), Beta-Blockers, Thyroid Hormones and Cholesterol Medications (Lipitor).

There is an unmet need for treatment of pain, especially periferal pain in animals, such as dogs, cats and horses, especially pain related to arthritis, such as osteoarthritis. There is a need for a treatment that has reduced side effect, such as gastrointestinal and renal toxicity.

WO2007/040982 discloses use of TT00, TT001 and/or TT002 in humans for treatment of neurological, psychiatric or pain disorders. IC50 bindings data in the mGluR receptor are shown as well as a study on the effect of TT00, TT001 or TT002 on TLESR in healthy dog in relation to food-intake. No results of the study are disclosed. No clinical data are present at all, especially no clinical data in association with pain treatment after administration of TT00, TT001 and/or TT002.

Rohof, et al., Aliment. Pharmacol. Ther. 2012, vol 35, pp 1231-1242, disclose a clinical study using TT001 to measure its effect on TLESR in healthy volunteers in association with food-intake. The results in FIGS. 2 and 4 show that only a high dose of 13 mg (about 0.19 mg/kg) has some effect at 2 to 3 hours after food-intake, but that there was no significant effect on reflux prior to food intake, nor at 1-2 hours after food intake. Some serious side effects associated with the high doses of 13 mg are mentioned. No clinical data are disclosed in association with pain treatment after administration of TT00, TT001 and/or TT002.

Combination Drug Therapy (CDT)

There are several studies looking at CDT for pain management.

Mao et al. J. Pain, 2011, vol 12, pp 157-166, discloses various combination drug therapies for treatment of pain. Most therapies use an opiate combined with another pain killer. mGluR5's are not mentioned at all for use in a combination therapy, such as pain treatment, or treatment of pain related to arthritis, such as osteoarthritis.

In the review, Mao J. et al, data are available for CDT in man but there is no information about treatment in animals, whatsoever. In Table 1, different combinations are listed and rated in terms of positive or negative results. It should be pointed out that for osteoarthritis, an orally combination of Tramadol and NSAIDs had a positive and better pain relief with add-on drug in man but that there is a study with the same CDT in dogs, where no additive clinical effect of the combination was reported.

In Table 1 from Mao et al, it is also mentioned that an orally combination of Tramadol and acetaminophen showed a positive and better pain relief with add-on drug in man. If this CDT was given to a cat, the toxicity might have killed it.

See also, Meunier N, et al., Randomised trial of perioperative tramadol for canine sterilisation pain management, Vet Rec. 2019 Oct. 5; 185(13): 406. doi: 10.1136/vr.105009. Epub 2019 Jul. 18, and Tanaka N, et al., cDNA cloning and characterization of feline CYP1A1 and CYP1A2, Life Sci. 2006 Nov. 25; 79(26): 2463-73. Epub 2006 Oct. 5.

There might be a general misconception that by just combining different drugs, there will be an additive effect. In Table 1 from Mao et al, one in four combinations do not give a positive result. There are even situations, where combinations are lowering the total efficacy of a pain treatment.

For a person skilled in the art, it is obvious that clinical results in different species do not translate automatically to other species. Therefore, a person skilled in the arts should and will suggest an independent evaluation of efficacy and toxicity for each species. This is clearly also the position of The Medical Products Agency in most countries.

There is an unmet need for treating pain using a safe, efficient and effective combination of drugs.

SUMMARY OF THE INVENTION

The present invention is directed to compounds TT00, TT001 and/or TT002, or a pharmaceutically acceptable salt thereof, diastereomer, enantiomer, isotope, pro-drug or metabolite or mixture thereof, for use in prevention and/or treatment of pain in dogs, cats or horses. In one aspect, the compound is TT001, or a hydrochloride or sulphate salt thereof. In another aspect, the compound is a hydrochloride salt of TT001. In a further aspect, the compound is a sulphate salt of TT001. In one aspect, the animal is a dog.

The characteristics and central working mechanism of compounds TT00, TT001 and/or TT002 make them a very different pain relief candidate compared to NSAIDs that are predominantly used today.

Compounds TT00, TT001 and/or TT002 show few side effects at the intended dose in dogs, cats and horses. They do not lose the potency over longer administration periods. Although compounds TT00, TT001 and/or TT002 are known to affect the central nervous system, they show a positive effect in treatment of peripheral pain, such as pain related to arthritis, such as osteoarthritis. Such pain may be chronical. TT00, TT001 and/or TT002 are believed to be effective, without incidence of any serious side effect, when used over a longer period, such as month or years. It is believed that TT00, TT001 and/or TT002 would have a reduced potential for side effects compared to conventional pain killing drugs used in animals today, such as NSAIDS, especially when treated over a longer period. The compounds of the invention are believed to have a reduced gastrointestinal and renal toxicity, especially compared to NSAIDs, in dogs, cats and horses.

In one aspect, pain is chronic pain. In another aspect, pain is peripheral pain. In a further aspect, pain is chronic and periferal pain. In an aspect, pain is pain related to arthritis, such as osteoarthritis. In another aspect, pain is chronic and periferal pain related to osteoarthritis.

The invention also relates to compounds TT00, TT001 and/or TT002, or a pharmaceutically acceptable salt thereof, diastereomer, enantiomer, isotope, pro-drug or metabolite or mixture thereof, for use in prevention and/or treatment of both a) pain, such as chronic and/or peripheral pain and/or pain related to arthritis, such as osteoarthritis and b) gastroesophageal reflux disease (GERD), in dogs, cats or horses.

In one aspect, pain is pain related to arthritis, such as osteoarthritis. In one aspect, the compound is TT001, or a hydrochloride or sulphate salt thereof. In an aspect, the animal is a dog. In another aspect, the animal is a cat or a horse. Because the compounds work on the central nervous system, they can be used to simulataneously treat and/or prevent pain and GERD.

The invention also relates to compounds TT00, TT001 and/or TT002, or a pharmaceutically acceptable salt thereof, diastereomer, enantiomer, isotope, pro-drug or metabolite or mixture thereof, for use in prevention and/or treatment of both a) pain, such as chronic and/or peripheral pain and/or pain related to arthritis, such as osteoarthritis and c) anxiety, in dogs, cats or horses. In one aspect, the animal is a horse. In one aspect, pain is pain related to arthritis, such as osteoarthritis. In another aspect, the animal is a cat or a dog. In one aspect, the compound is TT001, or a hydrochloride or sulphate salt thereof. Because the compounds work on the central nervous system, they can be used to simulataneously treat and/or prevent pain and anxiety. This is important prior to and during veterinary treatments of the animals, such as injections or operations.

The invention relates to a method of treating, preventing or reducing the risk of pain, such as chronic and/or periferal pain and/or pain related to arthritis, such as osteoarthritis, or both a) said pain combined with b) GERD or c) anxiety, which comprises administering to a dog, cat or horse, in need thereof, a therapeutically effective amount of compounds TT00, TT001 and/or TT002, or a pharmaceutically acceptable salt thereof, diastereomer, enantiomer, isotope, pro-drug or metabolite or mixture thereof. In one aspect, the compound is TT001, or a hydrochloride or sulphate salt thereof.

The invention further relates to a pharmaceutical composition comprising compounds TT00, TT001 and/or TT002, or a pharmaceutically acceptable salt thereof, diastereomer, enantiomer, isotope, pro-drug or metabolite or mixture thereof, in the association with a pharmaceutically acceptable adjuvant, diluent or carrier. In one aspect, the compound is TT001, or a hydrochloride or sulphate salt thereof.

The invention also relates to a process for the preparation of a pharmaceutical composition, as defined above, which comprises mixing compounds TT00, TT001 and/or TT002, or a pharmaceutically acceptable salt thereof, diastereomer, enantiomer, isotope, pro-drug or metabolite or mixture thereof, with a pharmaceutically acceptable adjuvant, diluent or carrier. In one aspect, the compound is TT001, or a hydrochloride or sulphate salt thereof.

One aspect relates to the pharmaceutical composition comprising compounds TT00, TT001 and/or TT002, or a pharmaceutically acceptable salt thereof, diastereomer, enantiomer, isotope, pro-drug or metabolite or mixture thereof, in the association with a pharmaceutically acceptable adjuvant, diluent or carrier, for use in prevention and/or treatment of pain, such as chronic and/or peripheral pain and/or pain related to arthritis, such as osteoarthritis, in dogs, cats or horses. In one aspect, pain is pain related to arthritis, such as osteoarthritis. In one aspect, the compound is TT001, or a hydrochloride or sulphate salt thereof. In an aspect, the animal is a dog. In another aspect, the animal is a cat or a horse.

One aspect relates to the pharmaceutical composition, comprising compounds TT00, TT001 and/or TT002, or a pharmaceutically acceptable salt thereof, diastereomer, enantiomer, isotope, pro-drug or metabolite or mixture thereof, in the association with a pharmaceutically acceptable adjuvant, diluent or carrier, for use in prevention and/or treatment of both a) pain, such as chronic and/or peripheral pain and/or pain related to arthritis, such as osteoarthritis and b) gastroesophageal reflux disease (GERD) in dogs, cats or horses. In one aspect, pain is pain related to arthritis, such as osteoarthritis. In one aspect, the compound is TT001, or a hydrochloride or sulphate salt thereof. In an aspect, the animal is a dog. In another aspect, the animal is a cat or a horse. In another aspect, pain is chronic and periferal pain related to osteoarthritis.

One aspect relates to the pharmaceutical composition, comprising compounds TT00, TT001 and/or TT002, or a pharmaceutically acceptable salt thereof, diastereomer, enantiomer, isotope, pro-drug or metabolite or mixture thereof, in the association with a pharmaceutically acceptable adjuvant, diluent or carrier, for use in prevention and/or treatment of both a) pain, such as chronic and/or peripheral pain and/or pain related to arthritis, such as osteoarthritis and c) anxiety in dogs, cats or horses. In one aspect, the compound is TT001, or a hydrochloride or sulphate salt thereof. In one aspect, pain is pain related to arthritis, such as osteoarthritis. In an aspect, the animal is a dog. In another aspect, the animal is a cat or a horse. In another aspect, pain is chronic and periferal pain related to osteoarthritis.

The invention also relates to the use of compounds TT00, TT001 and/or TT002, or a pharmaceutically acceptable salt thereof, diastereomer, enantiomer, isotope, pro-drug or metabolite or mixture thereof, in the manufacture of a medicament for the pain, such as chronic and/or periferal pain and/or pain related to arthritis, such as osteoarthritis, or both a) said pain combined with b) GERD or c) anxiety in dogs, cats or horses. In one aspect, said pain is pain related to arthritis, such as osteoarthritis. In one aspect, the compound is TT001, or a hydrochloride or sulphate salt thereof. In an aspect, the animal is a dog. In another aspect, the animal is a cat or a horse.

Compounds TT00, TT001 and/or TT002 may be administered at a dose of 0.1 to 5.0 mg/kg, or 0.1 to 2.0 mg/kg, or 0.1 to 1.0 mg/kg per day. One aspect relates to a dosage regime, wherein compounds TT00, TT001 and/or TT002 are administered to an animal at a dose of 0.1 to 5.0 mg/kg once daily, or twice daily. In one aspect, the compound is TT001, or a hydrochloride or sulphate salt thereof. In an aspect, the dose is for prevention and/or treatment in a dog.

In one aspect, the dosage regime is administration of compounds TT00, TT001 and/or TT002 at a dose of 0.1 to 1.0 mg/kg once daily. In one aspect, the dosage regime is administration of compounds TT00, TT001 and/or TT002 at a dose of 0.1 to 0.5 mg/kg twice daily. In one aspect, the compound is TT001, or a hydrochloride or sulphate salt thereof.

As mentioned above, there is no disclosure of pain treatment in dogs, cats and horses using mGluR5 antagonists. Even in the TLESR studies, there is no mention of effect of the compounds on pain relieve. Clinical studies in man have been discontinued.

The prevention and/or treatment of pain related pathology defined herein may be applied as a sole preventing and/or therapy or may involve, in addition to TT00, TT001 and/or TT002, conjoint treatment with conventional therapy of value in preventing and/or treating one or more disease conditions referred to herein. Such conventional therapy may include one or more of the following categories of agents: NSAIDs, anesthetics and opiates. It is believed that TT00, TT001 and/or TT002 in combination with other pain killers, may have a synergistic effect on pain relieve in an animal as well as an additive effect by dual treatment of different disease conditions.

In an aspect, NSAIDs are selected from the group comprising or consisting of the class of pyrazolidines that is 1,2-diphenylpyrazolidine-3,5-dione carrying a butyl group at the 4-position. It has a role as a non-narcotic analgesic, a non-steroidal anti-inflammatory drug, an antirheumatic drug, a peripheral nervous system drug, a metabolite and an EC 1.1.1.184 [carbonyl reductase (NADPH)] inhibitor. In another aspect, NSAIDs are selected from the group comprising or consisting of butyl pyrazolidines, oxicams, propionic acid derivative, fenamic acid, coxibs and other non-steroidal anti-inflammatory and antirheumatic agents. In a further aspect, NSAIDs are selected from the group comprising or consisting of oxicams, propionic acid derivatives and coxibs.

Opiates may be selected from the group comprising or consisting of tramadol or tapentadol.

Such conjoint treatment may be achieved by way of the simultaneous, sequential or separate dosing of the individual components of the treatment. Such combination products employ compounds TT00, TT001 and/or TT002, or a pharmaceutically acceptable salt thereof, diastereomer, enantiomer, isotope, pro-drug or metabolite or mixture thereof, for use in prevention and/or treatment of pain, such as chronic and/or periferal pain and/or pain related to arthritis, such as osteoarthritis in dogs, cats or horses.

In one aspect, the invention relates to a pharmaceutical composition comprising (i) compounds TT00, TT001 and/or TT002, or a pharmaceutically acceptable salt thereof, diastereomer, enantiomer, isotope, pro-drug or metabolite or mixture thereof, (ii) an additional therapeutic agent, or a pharmaceutically acceptable salt thereof, and (iii) a pharmaceutically acceptable excipient, carrier or diluent, for use in prevention and/or treatment of pain, such as chronic and/or periferal pain and/or pain related to arthritis, such as osteoarthritis, in dogs, cats or horses. In one aspect, pain is pain related to arthritis, such as osteoarthritis. In another aspect, pain is chronic and periferal pain related to osteoarthritis. In one aspect, the compound is TT001, or a hydrochloride or sulphate salt thereof. In an aspect, the animal is a dog. In another aspect, the animal is a cat or a horse.

In one aspect, the invention relates to a pharmaceutical composition comprising (i) compounds TT00, TT001 and/or TT002, or a pharmaceutically acceptable salt thereof, diastereomer, enantiomer, isotope, pro-drug or metabolite or mixture thereof, (ii) an additional therapeutic agent, or a pharmaceutically acceptable salt thereof, and (iii) a pharmaceutically acceptable excipient, carrier or diluent, for use in prevention and/or treatment of pain related to arthritis, such as osteoarthritis, in dogs, cats or horses. In an aspect, the pain is chronical pain related to arthritis, such as osteoarthritis. In one aspect, the invention relates to a pharmaceutical composition comprising (i) compounds TT00, TT001 and/or TT002, or a pharmaceutically acceptable salt thereof, diastereomer, enantiomer, isotope, pro-drug or metabolite or mixture thereof, (ii) an additional therapeutic agent, or a pharmaceutically acceptable salt thereof, and (iii) a pharmaceutically acceptable excipient, carrier or diluent, for use in prevention and/or treatment of both a) pain, such as chronic and/or peripheral pain and/or pain related to arthritis, such as osteoarthritis, and b) gastroesophageal reflux disease (GERD) in dogs, cats or horses. In one aspect, pain is pain related to arthritis, such as osteoarthritis. In another aspect, pain is chronic and periferal pain related to osteoarthritis. In one aspect, the compound is TT001, or a hydrochloride or sulphate salt thereof. In an aspect, the animal is a dog. In another aspect, the animal is a cat or a horse.

Anesthetics, such as acepromazine, have muscle relaxing properties that affect the lower esophageal sphincter (LES), causing more episodes of reflux during anesthesia. Co-treatment of an anesthetic with TT00, TT001 and/or TT002 may improve the condition of the animal, at least in association with a veterinary treatment, such as an operation.

In one aspect, the invention relates to a pharmaceutical composition comprising (i) compounds TT00, TT001 and/or TT002, or a pharmaceutically acceptable salt thereof, diastereomer, enantiomer, isotope, pro-drug or metabolite or mixture thereof, (ii) an additional therapeutic agent, or a pharmaceutically acceptable salt thereof, and (iii) a pharmaceutically acceptable excipient, carrier or diluent, for use in prevention and/or treatment of both a) pain, such as chronic and/or peripheral pain and/or pain related to arthritis, such as osteoarthritis, and c) anxiety in dogs, cats or horses. In one aspect, pain is pain related to arthritis, such as osteoarthritis. In another aspect, pain is chronic and periferal pain related to osteoarthritis. In one aspect, the compound is TT001, or a hydrochloride or sulphate salt thereof. In an aspect, the animal is a dog. In another aspect, the animal is a cat or a horse. Although TT00, TT001 and/or TT002 are believed to treat both pain and anxiety, it may be advantageous to combine TT00, TT001 and/or TT002 with an additional drug to improve the condition of the animal. Also, as mentioned above, in combination with anesthetics, TT00, TT001 and/or TT002 may improve the condition of the animal, prior to, during and after a veterinary treatment, such as an operation. Compounds TT00, TT001 and/or TT002 are believed to have a positive effect in GERD. It might even be a possibility to use compounds TT00, TT001 and/or TT002 in a combination treatment with NSAIDs as it has shown to influence GERD, which may be a serious side effect of NSAIDs. Because TT00, TT001 and/or TT002 act from the central nervous system and NSAIDs act peripheral, a combination of the two may have a synergistic effect on pain relieve in an animal, especially in dogs. In one aspect, the compound is TT001, or a hydrochloride or sulphate salt thereof.

In one aspect, the additional therapeutic agent is an NSAID, such as butyl pyrazolidines, oxicams, propionic acid derivative, fenamic acid or coxibs. In a further aspect, NSAIDs are selected from the group comprising or consisting of oxicams, propionic acid derivatives and coxibs. In one aspect, the additional therapeutic agent is any other non-steroidal anti-inflammatory. In a further aspect, NSAIDs is an antirheumatic agent. In one aspect, the additional therapeutic agent is an opiate, such as Tramadol or Tapentadol. In one aspect, the additional therapeutic agent is an anesthetic, such as acepromazine, morphine or propofol.

In another embodiment, the invention relates to a pharmaceutical composition comprising (i) compounds TT00, TT001 and/or TT002, or a pharmaceutically acceptable salt thereof, diastereomer, enantiomer, isotope, pro-drug or metabolite or mixture thereof, (ii) at least one additional therapeutic agent selected from the group comprising or consisting of anesthetics, NSAIDs and opiates, and (iii) a pharmaceutically acceptable excipient, carrier or diluent, for use in prevention and/or treatment of pain, such as chronic and/or periferal pain and/or pain related to arthritis, such as osteoarthritis, or prevention and/or treatment of both a) said pain combined with b) GERD or c) anxiety, in dogs, cats or horses. In one aspect, pain is pain related to arthritis, such as osteoarthritis. In another aspect, pain is chronic and periferal pain related to osteoarthritis. In one aspect, the compound is TT001, or a hydrochloride or sulphate salt thereof. In an aspect, the animal is a dog. In another aspect, the animal is a cat or a horse.

In another embodiment, the invention relates to a pharmaceutical composition comprising (i) compounds TT00, TT001 and/or TT002, or a pharmaceutically acceptable salt thereof, diastereomer, enantiomer, isotope, pro-drug or metabolite or mixture thereof, (ii) at least one additional therapeutic agent, which is an NSAID selected from the group comprising or consisting of oxicams, propionic acid derivative, and coxibs, and (iii) a pharmaceutically acceptable excipient, carrier or diluent, for use in prevention and/or treatment of pain, such as chronic and/or periferal pain and/or pain related to arthritis, such as osteoarthritis, or prevention and/or treatment of both a) said pain combined with b) GERD or with c) anxiety. In one aspect, pain is pain related to arthritis, such as osteoarthritis. In another aspect, pain is chronic and periferal pain related to osteoarthritis. In one aspect, the compound is TT001, or a hydrochloride or sulphate salt thereof. In an aspect, the animal is a dog. In another aspect, the animal is a cat or a horse.

In another embodiment, the invention relates to a pharmaceutical composition comprising (i) compounds TT00, TT001 and/or TT002, or a pharmaceutically acceptable salt thereof, diastereomer, enantiomer, isotope, pro-drug or metabolite or mixture thereof, (ii) at least one additional therapeutic agent, which is an other non-steroidal anti-inflammatory or an antirheumatic agent, and (iii) a pharmaceutically acceptable excipient, carrier or diluent, for use in prevention and/or treatment of pain, such as chronic and/or periferal pain and/or pain related to arthritis, such as osteoarthritis, or prevention and/or treatment of both a) said pain combined with b) GERD or with c) anxiety. In one aspect, pain is pain related to arthritis, such as osteoarthritis. In another aspect, pain is chronic and periferal pain related to osteoarthritis. In one aspect, the compound is TT001, or a hydrochloride or sulphate salt thereof. In an aspect, the animal is a dog. In another aspect, the animal is a cat or a horse.

In another embodiment, the invention relates to a pharmaceutical composition comprising (i) compounds TT00, TT001 and/or TT002, or a pharmaceutically acceptable salt thereof, diastereomer, enantiomer, isotope, pro-drug or metabolite or mixture thereof, (ii) at least one additional therapeutic agent, which is an opiate selected from the group comprising or consisting of tramadol and tapentadol and (iii) a pharmaceutically acceptable excipient, carrier or diluent, for use in prevention and/or treatment of pain, such as chronic and/or periferal pain and/or pain related to arthritis, such as osteoarthritis, or prevention and/or treatment of both a) said pain combined with b) GERD or with c) anxiety. In one aspect, pain is pain related to arthritis, such as osteoarthritis. In another aspect, pain is chronic and periferal pain related to osteoarthritis. In one aspect, the compound is TT001, or a hydrochloride or sulphate salt thereof. In an aspect, the animal is a dog. In another aspect, the animal is a cat or a horse.

In another embodiment, the invention relates to a pharmaceutical composition comprising (i) compounds TT00, TT001 and/or TT002, or a pharmaceutically acceptable salt thereof, diastereomer, enantiomer, isotope, pro-drug or metabolite or mixture thereof, (ii) at least one the additional therapeutic agent, which is an anesthetic selected from the group comprising or consisting of acepromazine, morphine or propofol, and (iii) a pharmaceutically acceptable excipient, carrier or diluent, for use in prevention and/or treatment of pain, such as chronic and/or periferal pain and/or pain related to arthritis, such as osteoarthritis, or prevention and/or treatment of both a) said pain combined with b) GERD or with c) anxiety. In one aspect, pain is pain related to arthritis, such as osteoarthritis. In another aspect, pain is chronic and periferal pain related to osteoarthritis. In one aspect, the compound is TT001, or a hydrochloride or sulphate salt thereof. In an aspect, the animal is a dog. In another aspect, the animal is a cat or a horse.

Such combination products employ the compounds TT00, TT001 and/or TT002 within the dosage range described herein and the other the additional therapeutic agent(s) within approved dosage ranges and/or the dosage described in the publication reference thereof.

The pharmaceutical composition comprising compounds TT00, TT001 and/or TT002, or a pharmaceutically acceptable salt thereof, diastereomer, enantiomer, isotope, pro-drug or metabolite or mixture thereof, optionally together with one or more additional therapeutic agent as defined above, may be administered topically or orally. In one aspect, the pharmaceutical composition is administered topically. In another aspect, the pharmaceutical composition is administered intramuscular. In a further aspect, the pharmaceutical composition is administered intravenously.

DETAILED DESCRIPTION OF THE INVENTION

The definitions set forth in this application are intended to clarify terms used throughout this application. The term "herein" means the entire application.

It is to be understood that the expression "compounds TT00, TT001 and/or TT002" includes pharmaceutically acceptable salt thereof, diastereomer, enantiomer, isotope, pro-drug or metabolite and the like, or mixture thereof, unless specified otherwise.

As used herein, "pharmaceutically acceptable salts" refer to forms of the disclosed compounds, wherein the parent compound is modified by making acid or base salts thereof. Examples of pharmaceutically acceptable salts include, but are not limited to, mineral or organic acid salts of basic residues such as amines; alkali or organic salts of acidic residues, such as carboxylic acids; and the like. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric acid. Examples of salts are hydrochloride salts or sulphate salts, especially 4-[5-[(1R)-1-[5-(3-Chlorophenyl)-3-isoxazolyl]ethoxy]-4-methyl-4H-1,2,4-triazol-3-yl]pyridine hydrochloride or 4-[5-[(1R)-1-[5-(3-Chlorophenyl)-3-isoxazolyl]ethoxy]-4-methyl-4H-1,2,4-triazol-3-yl]pyridine sulphate.

As used herein, the phrase "or pharmaceutically acceptable salts" include hydrates and solvates thereof.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like diethyl ether, ethyl acetate, ethanol, isopropanol, or acetonitrile are used.

Compounds TT00, TT001 and/or TT002, especially TT001, may exist in particular geometric or stereoisomeric forms. The present invention takes into account all such compounds, including tautomers, R- and S-enantiomers, diastereomers, (D)-isomers, (L)-isomers, the racemic mixtures thereof, and other mixtures thereof, as being covered within the scope of this invention.

As used herein, "tautomer" means other structural isomers that exist in equilibrium resulting from the migration of a hydrogen atom. For example, keto-enol tautomerism occurs where the resulting compound has the properties of both a ketone and an unsaturated alcohol.

Compounds TT00, TT001 and/or TT002, especially TT001, and salts described in this specification may be isotopically labelled (or "radio-labelled"). In that instance, one or more atoms are replaced by an atom having an atomic mass or mass number different from the atomic mass or mass number typically found in nature (i.e., naturally occurring). Examples of suitable isotopes that may be incorporated include $^2H$ (also written as "D" for deuterium), $^3H$ (also written as "T" for tritium), $^{11}C$, $^{13}C$, $^{14}C$, $^{13}N$, $^{15}N$, $^{15}O$, $^{17}O$, $^{18}O$ $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is used will depend on the specific application of that radio-labelled derivative. For example, for in vitro receptor labelling and competition assays, compounds that incorporate $^3H$ or $^{14}C$ are often useful. For radio-imaging applications $^{11}C$ or $^{18}F$ are often useful. In some embodiments, the radionuclide is $^3H$. In some embodiments, the radionuclide is $^{14}C$. In some embodiments, the radionuclide is $^{11}C$. And in some embodiments, the radionuclide is $^{18}F$. The present invention includes any isotope of TT00, TT001 and/or TT002 for use in diagnosis on animals, such as dogs, cats or horses.

Compounds TT00, TT001 and/or TT002, especially TT001, may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints. Said compounds may be administered topically.

The optimum dosage and frequency of administration will depend on the particular condition being treated and its severity; the species; the age, sex, size and weight, diet, and general physical condition of the particular animal; other medication the animal may be taking; the route of administration; the formulation; and various other factors known to physicians and others skilled in the art.

Dosages can be readily ascertained by those skilled in the art from this disclosure and the knowledge in the art. Thus, the skilled artisan can readily determine the amount of compound and optional additives, vehicles, and/or carriers in compositions and to be administered in methods of the invention.

The quantity of the compounds TT00, TT001 and/or TT002, especially TT001, to be administered will vary for the dog, cat or horse being treated and will vary from about 0.01 ng/kg of body weight to 10 mg/kg of body weight per day. Compounds TT00, TT001 and/or TT002 may be administered at a dose of 0.1 to 5.0 mg/kg, or 0.1 to 2.0 mg/kg, or 0.1 to 1.0 mg/kg per day. One aspect relates to a dosage regime, wherein compounds TT00, TT001 and/or TT002 are administered to a dog, cat or horse at a dose of 0.1 to 5.0 mg/kg once daily, or twice daily. In one aspect, the compound is TT001, or a hydrochloride or sulphate salt thereof.

In one aspect, the dosage regime is administration of compounds TT00, TT001 and/or TT002 at a dose of 0.1 to 1.0 mg/kg once daily, or 0.1 to 0.5 mg/kg twice daily, to a dog, cat or horse.

For preparing pharmaceutical compositions from the compounds TT00, TT001 and/or TT002, especially TT001, inert, pharmaceutically acceptable carriers can be either solid or liquid. Solid form compositions include powders, tablets, dispersible granules, capsules, cachets, and suppositories. A solid carrier can be one or more substances, which may also act as diluents, flavoring agents, solubilizers, lubricants, suspending agents, binders, or tablet disintegrating agents; it can also be an encapsulating material.

Liquid form compositions include ointments, creams, gels, aqeuous liquids, which may be formulated inside a transdermal patch.

A process for preparation of a capsule may comprise the following steps;
a) Mixing compound TT00, TT001 or TT002, especially TT001 together with additives, such as calcium hydrogen, phosphate and hydroxy propylcellulose and stir for a period of time,
b) Adding further additives, such as mannitol and croscarmellose sodium,
c) Adding water and granulating the mixture,
d) Drying the obtained granulate,
e) Milling the dried granulate,
f) Adding further additives, such as sodium stearyl fumarate,
g) Mixing the obtained mixture, and
h) Filling of the mixture in capsules, or pressing the mixture into tablets.

The pharmaceutical composition may be used in prevention and/or treatment of any disease condition or combination of conditions mentioned herein.

Combination Therapies

The prevention and/or treatment of pain related pathology defined herein may be applied together with conventional therapy of value in preventing and/or treating one or more disease conditions referred to herein. Such conventional therapy may include one or more of the following categories of additional therapeutic agents: NSAIDs, anesthetics and opiates.

Examples of NSAIDs may be NSAIDs selected from the group comprising or consisting of the class of pyrazolidines that is 1,2-diphenylpyrazolidine-3,5-dione carrying a butyl group at the 4-position. It has a role as a non-narcotic analgesic, a non-steroidal anti-inflammatory drug, an antirheumatic drug, a peripheral nervous system drug, a metabolite and an EC 1.1.1.184 [carbonyl reductase (NADPH)] inhibitor. In another aspect, NSAIDs are selected from the group comprising or consisting of butyl pyrazolidines, oxicams, propionic acid derivative, fenamic acid and coxibs. The NSAIDs may be selected from the group comprising or consisting of oxicams, propionic acid derivatives and coxibs.

The NSAIDs may include butyl pyrazolidines, oxicams, propionic acid derivative or coxibs. The additional therapeutic agent may be any other non-steroidal anti-inflammatory or antirheumatic agents.

Examples of opiates may include tramadol and tapentadol.

Such conjoint treatment may be achieved by way of the simultaneous, sequential or separate dosing of the individual components for use in prevention and/or treatment of pain, such as chronic and/or periferal pain and/or pain related to arthritis, such as osteoarthritis in dogs, cats or horses.

The combination may comprise or consist of a pharmaceutical composition comprising (i) compounds TT00, TT001 and/or TT002, or a pharmaceutically acceptable salt thereof, diastereomer, enantiomer, isotope, pro-drug or metabolite or mixture thereof, (ii) an additional therapeutic agent, or a pharmaceutically acceptable salt thereof, and (iii) a pharmaceutically acceptable excipient, carrier or diluent.

The combination may also comprise or consist of a pharmaceutical composition comprising (i) compounds TT00, TT001 and/or TT002, or a pharmaceutically acceptable salt thereof, diastereomer, enantiomer, isotope, pro-drug or metabolite or mixture thereof, (ii) at least one additional therapeutic agent selected from the group consisting of anesthetic, NSAID and opiates, and (iii) a pharmaceutically acceptable excipient, carrier or diluent.

This definition of the combination includes a pharmaceutical composition comprising (i) compounds TT00, TT001 and/or TT002, or a pharmaceutically acceptable salt thereof, diastereomer, enantiomer, isotope, pro-drug or metabolite or mixture thereof, and a pharmaceutically acceptable excipient, carrier or diluent, and (ii) at least one additional therapeutic agent selected from the group consisting of anesthetic, NSAID and opiates, and a pharmaceutically acceptable excipient, carrier or diluent.

The combination may be (i) TT001, or a hydrochloride or sulphate salt thereof and (ii) acepromazine.

The combination may be (i) TT001, or a hydrochloride or sulphate salt thereof and (ii) oxicams. The combination may be (i) TT001, or a hydrochloride or sulphate salt thereof and (ii) propionic acid derivatives. The combination may be (i) TT001, or a hydrochloride or sulphate salt thereof and (ii) coxibs.

The additional therapeutic agent may be an opiate, such as tramadol and tapentadol.

The combination may be (i) TT001, or a hydrochloride or sulphate salt thereof and (ii) tramadol. The combination may be (i) TT001, or a hydrochloride or sulphate salt thereof and (ii) tapentadol.

The additional therapeutic agent may be an anesthetic selected from the group comprising or consisting of acepromazine, morphine or propofol.

The combination may be (i) TT001, or a hydrochloride or sulphate salt thereof and (ii) acepromazine. The combination may be (i) TT001, or a hydrochloride or sulphate salt thereof and (ii) morphine. The combination may be (i) TT001, or a hydrochloride or sulphate salt thereof and (ii) propofol.

The combination may be for use in prevention and/or treatment of pain, such as chronic and/or periferal pain and/or pain related to arthritis, such as osteoarthritis, or prevention and/or treatment of both a) said pain combined with b) GERD or c) anxiety.

Pharmaceutical Composition
Ointment
Active corresponding to TT001 Weight: 0.1 to 50 mg
propylene carbonate weight: 50 mg
paraffin, hard weight: 30 mg
beeswax white weight: 35 mg
paraffin, liquid weight: 110 mg
paraffin, white soft weight: 774.7 mg
Cream
TT001 Weight: 0.1-100 mg
propylene glycol weight: 100 mg
isopropyl myristate weight: 50 mg
cetostearyl alcohol weight: 52.5 mg
citric acid, monohydrate (e330) weight: 0.5 mg
disodium phosphate, anhydrous weight: 0.6 mg
water weight: a sufficient amount is added to achieve the target weight of 30 or 100 g
paraffin, liquid weight: 400 mg
macrogol cetostearyl ether weight: 7.5 mg
disodium phosphate dodecahydrate (e339) weight: 1.5 mg
imidurea weight: 2 mg
Capsule

TABLE 1

Components and quantities for TT001 Capsules 2 mg and 8 mg

| Components | 2 mg | 8 mg | Function | Standard |
| --- | --- | --- | --- | --- |
| TT001 | 2 mg | 8 mg | Drug Substance | AstraZeneca |
| Calcium hydrogen phosphate dehydrate/ Dibasic Calcium Phosphate Dihydrate | 70.5 mg | 68.5 mg | Filler | Ph Eur or USP |
| Hydroxypropylcellulose/ Hydroxypropyl Cellulose | 12 mg | 12 mg | Binder | Ph Eur or NF |
| Mannitol | 141.1 mg | 137.1 mg | Filler | Ph Eur or USP |
| Croscarmellose sodium | 9.6 mg | 9.6 mg | Disintegrant | Ph Eur or NF |
| Sodium stearyl fumarate | 4.8 mg | 4.8 mg | Lubricant | Ph Eur or NF |
| Water, purified/ Purified water[a] | q.s. | q.s. | Granulation liquid | Ph Eur or USP |
| Capsules | 1 capsule | 1 capsule | Capsule | JP |

Preparation of Compounds
Compounds TT00, TT001 and/or TT002 can be prepared as a free base or a pharmaceutically acceptable salt thereof by the processes described in U.S. Pat. No. 7,476,684 B2 or WO2007/040982 A1, which are hereby included by reference.
Pharmaceutical Composition
Formulation Method for the Preparation of TT001 for I.V. Dosing, 0.1 to 10 mg/ml
The formulation method is applicable at concentrations in formulation between 0.1 and 10 mg/mL corresponding to 0.262 and 26.2 μmol/mL
TT001 M.W.: 381.8 g/mol
The dissolution of TT001 is moderate, allow a couple of hours for complete dissolution.
Vehicle
Preparation of 40% w/v HPβCD solution in water for injection
Excipients Hydroxypropyl-β-cyclodextrin, Kleptose, Roquette (HPβCD) 400 mg (40% w/v)
Water for injection to 1 ml (1.13 g)
Appearance Clear
Density 1.13 g/cm3
Formulation
Preparation of TT001 I.V. formulations between 0.1 and 10 mg/ml
TT001 parent form 0.1-10 mg
Vehicle (40% w/v HPβCD solution in water for injection) to 1 ml (1.13 g)
Appearance Clear
Density 1.13 g/cm$^3$
Comments
The dissolution of TT001 is moderate, allow a couple of hours for complete dissolution.
Ointment
Active corresponding to TT001 Weight: 0.1 to 50 mg
propylene carbonate weight: 50 mg
paraffin, hard weight: 30 mg
beeswax white weight: 35 mg
paraffin, liquid weight: 110 mg
paraffin, white soft weight: 774.7 mg
Cream
TT001 Weight: 0.1-100 mg
propylene glycol weight: 100 mg
isopropyl myristate weight: 50 mg
cetostearyl alcohol weight: 52.5 mg
citric acid, monohydrate (e330) weight: 0.5 mg
disodium phosphate, anhydrous weight: 0.6 mg
water weight: a sufficient amount is added to achieve the target weight of 30 or 100 g
paraffin, liquid weight: 400 mg
macrogol cetostearyl ether weight: 7.5 mg
disodium phosphate dodecahydrate (e339) weight: 1.5 mg
imidurea weight: 2 mg
Capsule

TABLE 1

Components and quantities for TT001 Capsules 2 mg and 8 mg

| Components | 2 mg | 8 mg | Function | Standard |
|---|---|---|---|---|
| TT001 | 2 mg | 8 mg | Drug Substance | AstraZeneca |
| Calcium hydrogen phosphate dehydrate/ Dibasic Calcium Phosphate Dihydrate | 70.5 mg | 68.5 mg | Filler | Ph Eur or USP |
| Hydroxypropylcellulose/ Hydroxypropyl Cellulose | 12 mg | 12 mg | Binder | Ph Eur or NF |
| Mannitol | 141.1 mg | 137.1 mg | Filler | Ph Eur or USP |
| Croscarmellose sodium | 9.6 mg | 9.6 mg | Disintegrant | Ph Eur or NF |
| Sodium stearyl fumarate | 4.8 mg | 4.8 mg | Lubricant | Ph Eur or NF |
| Water, purified/ Purified water$^a$ | q.s. | q.s. | Granulation liquid | Ph Eur or USP |
| Capsules | 1 capsule | 1 capsule | Capsule | JP |

EXAMPLES

Pharmaceutical Composition
Ointment
TT001 Weight: 0.1-100 mg
propylene carbonate weight: 50 mg
paraffin, hard weight: 30 mg
beeswax white weight: 35 mg
paraffin, liquid weight: 110 mg
paraffin, white soft weight: 774.7 mg
Cream
TT001 Weight: 0.1-100 mg
propylene glycol weight: 100 mg
isopropyl myristate weight: 50 mg
cetostearyl alcohol weight: 52.5 mg
citric acid, monohydrate (e330) weight: 0.5 mg
disodium phosphate, anhydrous weight: 0.6 mg
water weight: a sufficient amount is added to achieve the target weight of 30 or 100 g
paraffin, liquid weight: 400 mg
macrogol cetostearyl ether weight: 7.5 mg
disodium phosphate dodecahydrate (e339) weight: 1.5 mg
imidurea Weight: 2 mg
Pain Relief Experiment
Protocols that may be used for assessment of pain relief in dogs are;
  Kinetic Data with Force Plates and a Pressure Walkway
  Helsinki chronic pain index (HCPI)
  Canine Brief Pain Inventory (CBPI)
  Cincinnaty Orthopedic Disability Index (CODI)
  Liverpool Osteoarthritis in Dogs (LOAD)

As chronic pain also will be assessed by the owner, so called "owner questionnaires" are very often used for the efficacy assessment of pain products.

Canine gait analysis is an important tool for objectively evaluating normal and abnormal gaits. While there are many methods for collecting the temporal and spatial parameters of gait analysis, currently force plates (FP) are considered the gold standard for measuring ground reaction forces (GRF) and related indices generated from those forces. The data collected from FP have proven to be an effective method for assessing lameness, as well as the success of medical or surgical interventions, or a combination, in dogs with musculoskeletal pathology.

Example 1

To be able to assess the pain, a validated pain model like, Kinetic Data with Force Plates and a or Pressure Walkway can be used. This should be combined with a validated pain protocol like, Helsinki chronic pain index (HCPI), Canine Brief Pain Inventory (CBPI) or Liverpool Osteoarthritis in Dogs (LOAD).

The Trial

To be included in the trial, the dog should suffer from OA and a veterinarian will decide if the dog should be included in the trial or not.

The owner will answer questions according to the protocol at the first meeting.

Then the owner's dog with OA are led on a pressure walkway with attached gyros on their legs and head. The pressure on the walkway is recorded as well as the data from the gyros. The walk is also video filmed.

A dog with OA will put more weight on the unaffected limb as it walks, this is recorded by both the pressure walkway and the gyros.

After the initial walk, the dogs will be medicated with TT001 prepared as an oral formulation or a local transdermal formulation and then sent home. After one week, the owner will bring back the dog. During that week, the dog has been medicated with TT001 by the owner.

At the second meeting, after one week, the dog will walk the walkway again. The owner will answer questions according to the protocol.

The third and last meeting is one week later, and the procedure will be the same as the previously week.

The data from the walkway, gyros and video are processed. The algorithm will compare the different data sets and present any differences in the gait of the dog. This will in turn be the basis for the evaluation of the effect of TT001 on pain.

This example is expected to show that TT001 actually has an effect on pain in dogs with OA and not the toxic effects that are known from NSAID.

Example 2

Toxic effects of NSAIDs are caused partly by inhibition of the production of prostaglandins that protect homeostasis of the kidneys and gastrointestinal tract. The cat is particularly susceptible to the toxic effects of some NSAIDs due to its deficiency of the hepatic glutathione-dependent enzyme system which is involved in metabolism of many of the NSAIDs. Toxic side-effects include: gastric irritation, progressing to vomiting, ulceration and hemorrhage, enteritis leading to diarrhea, blood dyscrasias, occasionally hepatotoxicity and/or nephrotoxicity. Nephrotoxicity is more likely in dehydrated, hypovolemic or hypotensive animals, those undergoing anesthesia, or in animals being treated with other drugs which are potentially nephrotoxic.

It should be understood that geriatric cats are more often affected by Osteoarthritis (OA) than younger cats and that these older cats have a much higher incidence of kidney problems. As the treatment of OA is lifelong it is important that the medication does not have any adverse effect on cat kidneys. TT001 has not shown any adverse effect on kidneys.

We intend to show in a clinical trial that cats with OA will receive pain relief after medicated with TT001.

To be able to assess the pain, a validated pain model like, Kinetic Data with Force Plates and a or Pressure Walkway can be used. This should be combined with a validated pain protocol like, Helsinki chronic pain index (HCPI), Canine Brief Pain Inventory (CBPI) or Liverpool Osteoarthritis in Dogs (LOAD).

The Trial

To be included in the trial, the cat should suffer from OA and a veterinarian will decide if the cat should be included in the trial or not.

The owner will answer questions according to the protocol at the first meeting.

Then the owner's cat with OA are led on a pressure walkway with attached gyros on their legs and head. The pressure on the walkway is recorded as well as the data from the gyros. The walk is also video filmed.

A cat with OA will put more weight on the unaffected limb as it walks, this is recorded by both the pressure walkway and the gyros.

After the initial walk, the cats will be medicated with TT001 prepared as an oral formulation or a local transdermal formulation and then sent home. After one week, the owner will bring back the cat. During that week, the cat has been medicated with TT001 by the owner.

At the second meeting, after one week, the cat will walk the walkway again. The owner will answer questions according to the protocol.

The third and last meeting is one week later, and the procedure will be the same as the previously week.

The data from the walkway, gyros and video are processed. The algorithm will compare the different data sets and present any differences in the gait of the cats. This will in turn be the basis for the evaluation of the effect of TT001 on pain.

This example is expected to show that TT001 actually has an effect on pain in cats with OA and not the toxic effects that are known from NSAID.

The invention claimed is:

1. A method of treating pain from osteoarthritis in a dog, comprising:
   administering to a dog in need thereof an effective amount of a compound selected from the group consisting of: 4-[5-[(rac)-1-[5-(3-Chlorophenyl)-3-isoxazolyl]ethoxy]-4-methyl-4H-1,2,4-triazol-3-yl]pyridine (TT00), 4-[5-[(1R)-1-[5-(3-Chlorophenyl)-3-isoxazolyl]ethoxy]-4-methyl-4H-1,2,4-triazol-3-yl]pyridine, (TT001) and 4-[5-[(1S)-1-[5-(3-Chlorophenyl)-3-isoxazolyl]ethoxy]-4-methyl-4H-1,2,4-triazol-3-yl]pyridine (TT002), and combinations thereof, or a pharmaceutically acceptable salt thereof, enantiomer, or mixture thereof;
   wherein said dog has osteoarthritis and the pain is a direct result of the osteoarthritis.

2. The method according to claim 1, wherein the pain is peripheral pain.

3. The method according to claim 1, wherein the pain is chronic pain.

4. The method according to claim 1, wherein said dog has gastroesophageal reflux disease (GERD) and
   wherein the administering treats the GERD.

5. The method according to claim 1, wherein said dog has anxiety and
   wherein the administering treats the anxiety.

6. A method of treating pain from osteoarthritis in a dog, comprising:
   administering to a dog in need thereof an effective amount of a compound selected from the group consisting of: 4-[5-[(rac)-1-[5-(3-Chlorophenyl)-3-isoxazolyl]ethoxy]-4-methyl-4H-1,2,4-triazol-3-yl]pyridine (TT00), 4-[5-[(1R)-1-[5-(3-Chlorophenyl)-3-isoxazolyl]ethoxy]-4-methyl-4H-1,2,4-triazol-3-yl]pyridine, (TT001) and/or 4-[5-[(1S)-1-[5-(3-Chlorophenyl)-3-isoxazolyl]ethoxy]-4-methyl-4H-1,2,4-triazol-3-yl]pyridine (TT002), and combinations thereof, or a pharmaceutically acceptable salt thereof, enantiomer, or mixture thereof, in combination with a pharmaceutically acceptable adjuvant, diluent or carrier
   wherein said dog has osteoarthritis and the pain is a direct result of the osteoarthritis.

7. The method according to claim 6,
   wherein said dog has gastroesophageal reflux disease (GERD) and
   wherein the administering treats the GERD.

8. The method according to claim 6, wherein the compound is administered in a pharmaceutical composition, comprising a pharmaceutically acceptable adjuvant, diluent or carrier,
   wherein said dog has anxiety, and
   wherein the administering treats the anxiety.

9. A method of treating pain from osteoarthritis in a subject dog comprising:
   administering a pharmaceutical composition comprising (i) compounds 4-[5-[(rac)-1-[5-(3-Chlorophenyl)-3-isoxazolyl]ethoxy]-4-methyl-4H-1,2,4-triazol-3-yl]pyridine (TT00), 4-[5-[(1R)-1-[5-(3-Chlorophenyl)-3-isoxazolyl]ethoxy]-4-methyl-4H-1,2,4-triazol-3-yl]pyridine, CAS Number 934282-55-0 (TT001) and/or 4-[5-[(1S)-1-[5-(3-Chlorophenyl)-3-isoxazolyl]ethoxy]-4-methyl-4H-1,2,4-triazol-3-yl]pyridine (TT002), or a pharmaceutically acceptable salt thereof, enantiomer, or mixture thereof, and a pharmaceutically acceptable excipient, carrier or diluent, and (ii) at least one additional therapeutic agent selected from the group consisting of anesthetic, NSAID and opiates, and a pharmaceutically acceptable excipient, carrier, and-diluent, for use in treatment of peripheral pain or chronic and peripheral pain related to osteoarthritis in dogs;
   wherein said dog has osteoarthritis and the pain is a direct result of the osteoarthritis.

10. A method of treating pain from osteoarthritis in a subject dog comprising:
    administering a pharmaceutical composition comprising (i) compounds 4-[5-[(rac)-1-[5-(3-Chlorophenyl)-3-isoxazolyl]ethoxy]-4-methyl-4H-1,2,4-triazol-3-yl]pyridine (TT00), 4-[5-[(1R)-1-[5-(3-Chlorophenyl)-3-isoxazolyl]ethoxy]-4-methyl-4H-1,2,4-triazol-3-yl]pyridine, (TT001) and/or 4-[5-[(1S)-1-[5-(3-Chlorophenyl)-3-isoxazolyl]ethoxy]-4-methyl-4H-1,2,4-triazol-3-yl]pyridine (TT002), or a pharmaceutically acceptable salt thereof, enantiomer, or mixture thereof, (ii) an additional therapeutic agent, or a pharmaceutically acceptable salt thereof, and (iii) a pharmaceutically acceptable excipient, carrier or diluent wherein said dog has osteoarthritis and the pain is a direct result of the osteoarthritis.

11. The method of claim 9:

wherein said dog has gastroesophageal reflux disease (GERD) and wherein the administering prevents and treats the GERD.

12. The method of claim 9 wherein said dog has anxiety, and wherein the administering treats the anxiety.

13. The method according to claim 10, wherein the additional therapeutic agent is an anesthetic, NSAID or opiate.

14. The method according to claim 9, wherein the additional therapeutic agent is an NSAID selected from the group comprising butyl pyrazolidines, oxicams, propionic acid derivative, fenamic acid and coxibs.

15. The method according to claim 9, wherein the additional therapeutic agent is an anesthetic selected from the group comprising acepromazine, morphine or propofol.

16. The method according to claim 9, wherein the additional therapeutic agent is an opiate.

17. The method according to claim 1, wherein the compound is TT001, or a hydrochloride or sulphate salt thereof.

18. The method according to claim 1, wherein the selected compound is administered to a dog at a dose of 0.1 to 5.0 mg/kg.

19. The method according to claim 1, wherein the selected compound is administered to a dog at a dose of 0.1 to 1.0 mg/kg, once daily.

20. The method according to claim 1, wherein the selected compound is administered to a dog at a dose of 0.1 to 0.5 mg/kg, twice daily.

21. The method according to claim 1, wherein compound TT001 is administered to a dog at a dose of 0.1 to 1.0 mg/kg, once daily.

* * * * *